US006953211B2

(12) United States Patent
Di Vinadio

(10) Patent No.: US 6,953,211 B2
(45) Date of Patent: Oct. 11, 2005

(54) ANTI-PANIC OPENING SYSTEM FOR DOORS

(75) Inventor: Aimone Balbo Di Vinadio, Turin (IT)

(73) Assignee: SAVIO S.p.A., Chiusa San Michele (Torino) (IT)

( * ) Notice: Subject to any disclaimer, the term of this patent is extended or adjusted under 35 U.S.C. 154(b) by 0 days.

(21) Appl. No.: 10/401,769

(22) Filed: Mar. 31, 2003

(65) Prior Publication Data

US 2003/0222461 A1 Dec. 4, 2003

(30) Foreign Application Priority Data

Mar. 29, 2002 (IT) ...................................... TO2002A0281

(51) Int. Cl.[7] .............................................. E05C 19/18
(52) U.S. Cl. ........................... 292/296; 292/92; 292/93; 292/94; 292/DIG. 65; 70/91; 70/92
(58) Field of Search ............................ 292/39, 296, 92, 292/93, 94, 21, 173, 188, 259 R, DIG. 65, 289, 244; 70/462, 91, 92, 93

(56) References Cited

U.S. PATENT DOCUMENTS

| | | | | |
|---|---|---|---|---|
| 1,097,372 A | * | 5/1914 | Stewart | 292/21 |
| 1,141,338 A | * | 6/1915 | Hill | 292/92 |
| 1,203,965 A | * | 11/1916 | Bogenberger | 292/21 |
| 1,898,505 A | * | 2/1933 | Soemer | 292/92 |
| 1,906,517 A | * | 5/1933 | Bishop | 292/92 |
| 2,824,440 A | * | 2/1958 | Gesing et al. | 70/92 |
| 2,887,336 A | * | 5/1959 | Meyer | 292/21 |
| 2,910,585 A | * | 10/1959 | Baring et al. | 327/336 |
| 2,945,372 A | * | 7/1960 | Reed | 70/92 |
| 3,097,007 A | * | 7/1963 | Eichacker et al. | 292/92 |
| 3,345,099 A | * | 10/1967 | Paul et al. | 292/21 |
| 3,435,643 A | * | 4/1969 | Pollak et al. | 70/92 |
| 3,705,739 A | * | 12/1972 | Adler | 292/92 |
| 3,819,213 A | * | 6/1974 | Vanderburgh | 292/21 |
| 3,945,670 A | * | 3/1976 | Peterson | 292/92 |
| 3,993,335 A | * | 11/1976 | Schmidt | 292/21 |
| 4,006,471 A | * | 2/1977 | Pappas | 340/542 |
| 4,083,590 A | * | 4/1978 | Folger | 292/92 |
| 4,130,306 A | * | 12/1978 | Brkic | 292/5 |
| 4,387,917 A | * | 6/1983 | Cocker | 292/40 |
| 4,458,928 A | * | 7/1984 | Hirschbein | 292/92 |
| 4,498,319 A | * | 2/1985 | Balducci et al. | 70/92 |
| 4,714,282 A | * | 12/1987 | Henderson | 292/36 |
| 4,839,988 A | * | 6/1989 | Betts et al. | 49/141 |
| 4,906,034 A | * | 3/1990 | Verslycken | 292/92 |
| 4,978,151 A | * | 12/1990 | Coleman et al. | 292/21 |
| 5,054,825 A | * | 10/1991 | Mangin et al. | 292/92 |
| 5,083,822 A | * | 1/1992 | Mangin et al. | 292/21 |
| 5,088,786 A | * | 2/1992 | Linder | 292/92 |
| 5,184,852 A | * | 2/1993 | O'Brien | 292/40 |
| 6,000,733 A | * | 12/1999 | Linder | 292/92 |
| 6,189,939 B1 | * | 2/2001 | Zehrung | 292/92 |
| 6,394,508 B1 | * | 5/2002 | Zehrung | 292/92 |
| 6,601,881 B2 | * | 8/2003 | Mandell et al. | 292/92 |

FOREIGN PATENT DOCUMENTS

GB          2039588       * 12/1979

* cited by examiner

Primary Examiner—Daniel P. Stodola
Assistant Examiner—Carlos Lugo
(74) Attorney, Agent, or Firm—Sughrue Mion, PLLC

(57) ABSTRACT

Anti-panic opening system for doors in which a lateral spring latch bolt (3) is actuated by an actuator assembly (10) including a first and a second movable actuating member (19, 20) designed to operate respectively in a first position in which the spring latch (3) protrudes from one side of a covering case (9) and in a second position, turned over by 180° relative to the first position, in which the spring latch (3) projects from the opposite side of the covering case (9).

3 Claims, 4 Drawing Sheets

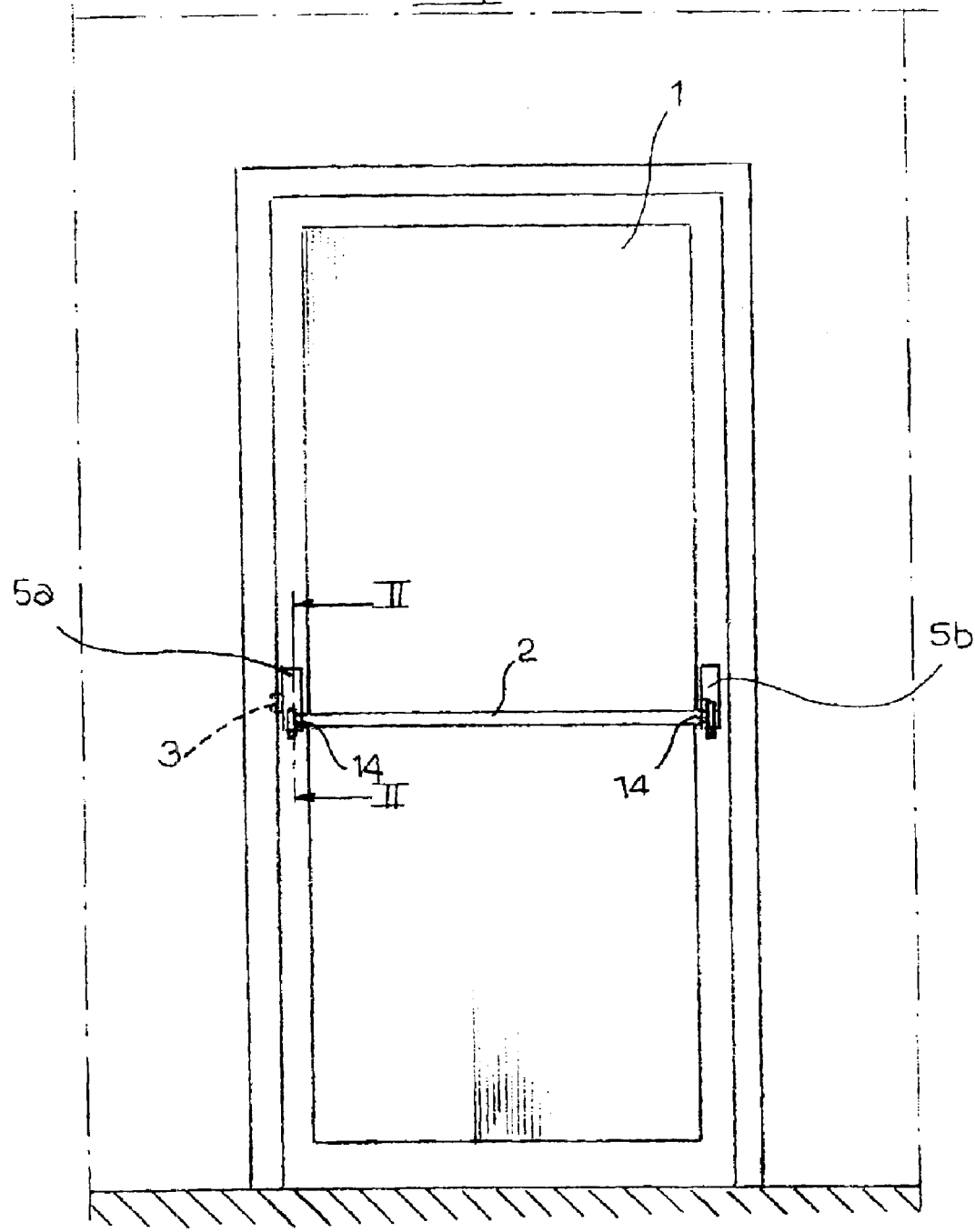

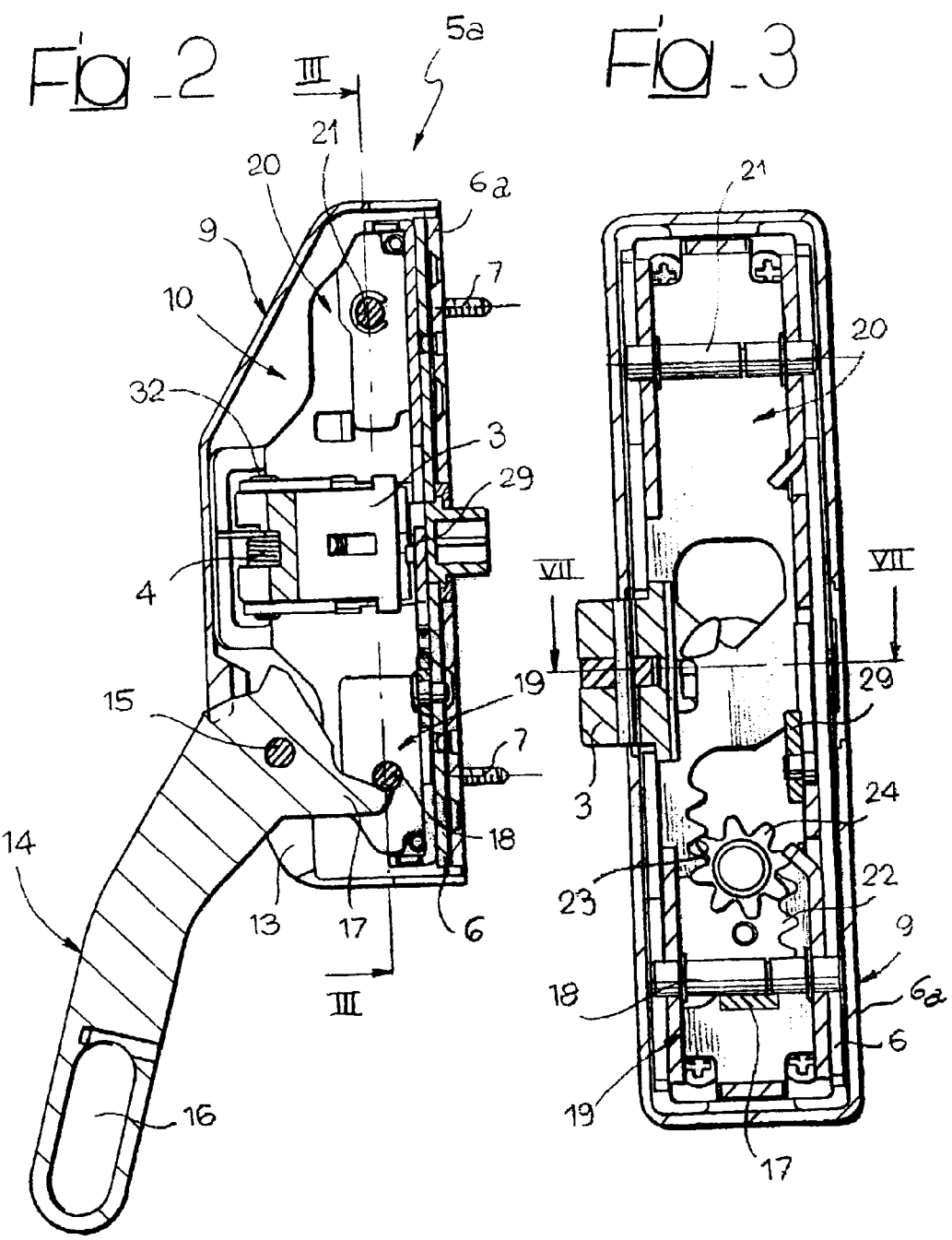

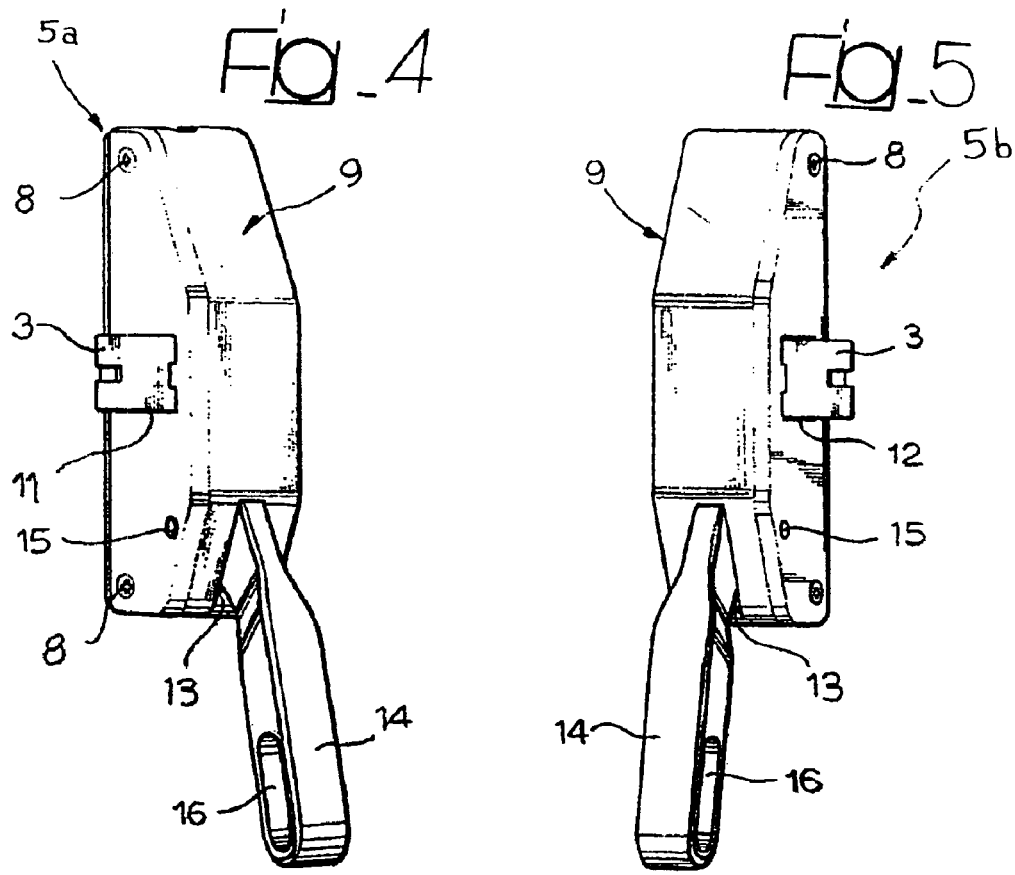
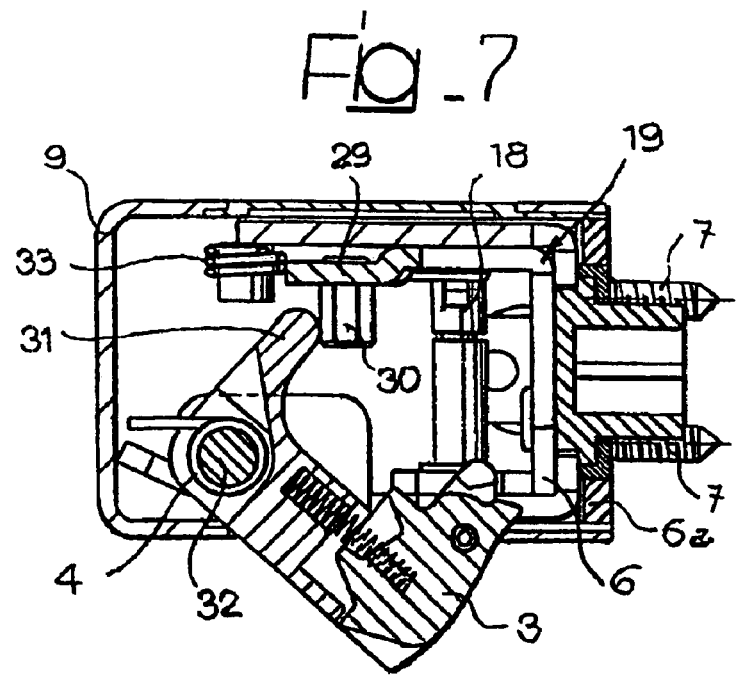

Fig_6
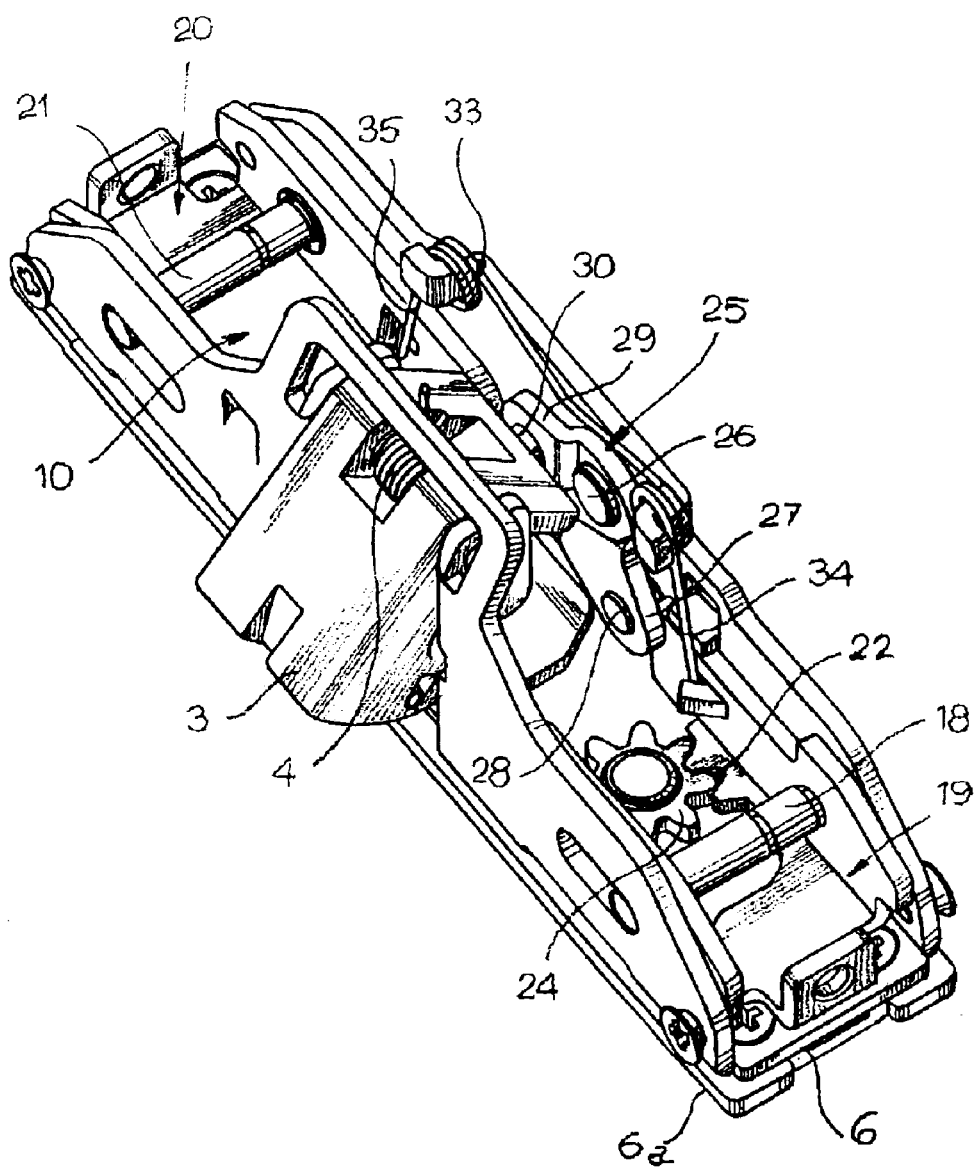

ANTI-PANIC OPENING SYSTEM FOR DOORS

FIELD OF THE INVENTION

The present invention relates to anti-panic opening systems for doors, of the type including a control bar applied transversely to the door wing and movable by a pushing action to actuate the opening of a lateral spring latch bolt between an extracted locking position and a recessed position to free the push opening of the door.

STATE OF THE PRIOR ART

In such anti-panic opening systems, the spring latch is traditionally operated by means of an actuator assembly housed within a covering case and including a control lever movable by means of the aforesaid bar. Depending on the direction of opening of the door wing, the spring latch bolt is positioned on the right side or on the left side of the door wing: currently, therefore, manufacturers of such systems must have provide two different actuator assemblies, a right one (with the bolt protruding on the right side) and a left one (with the bolt protruding on the left side) so the installer can employ the required one on each occasion. The unneeded actuator assembly is then hidden in its covering case before the application thereof in correspondence with the hinging side of the door wing.

This arrangement obviously entails additional production costs and a certain degree of complication for installers.

SUMMARY OF THE INVENTION

The object of the present invention is in fact to overcome such drawbacks.

According to the invention, this object is achieved thanks to the fact that an anti-panic opening system for doors of the type defined above is essentially characterised in that:

said actuator includes a first and a second movable actuating member designed to operate respectively in a first position in which the spring latch protrudes from one side of the covering case and in a second position, turned over by 180° relative to said first position, in which the spring latch protrudes from the opposite side of the covering case, the control lever is connected in articulated fashion to the covering case, and the covering case can be coupled on said actuator assembly selectively in one or in the other of said first and second position thereof and has two lateral openings usable correspondingly for the passage of the spring latch.

Thanks to this solution idea, a dual advantage is obtained: on one hand, the manufacturer of the system can reduce the cost of fabricating the system, having eliminated the need to provide a second actuator assembly destined, in conventional system, to be eventually eliminated. On the other hand, system installation operations are considerably simplified.

According to a preferred embodiment of the invention, the first and the second movable member of the actuator assembly consist of a pair of opposite cursors mounted able to slide along a guiding support of the actuator assembly and cinematically coupled in such a way that to the translation of one of said cursors in a direction corresponds the translation of the other one of said cursors in the opposite direction; each of the two cursors being provided with a respective abutment element able to co-operate with the control lever.

BRIEF DESCRIPTION OF THE DRAWINGS

The invention will now be described in detail with reference to the accompanying drawings, provided purely by way of non limiting example, in which:

FIG. 1 is a schematic lateral elevation view of a door provided with an anti-panic opening system according to the invention, FIG. 2 is a vertical section and enlarged scale view according to the line II—II of FIG. 1, FIG. 3 is a vertical section and enlarged scale view according to the line III—III of FIG. 2, FIG. 4 is a perspective, reduced scale view of FIG. 2, FIG. 5 is a similar view to FIG. 4 in an alternative condition of application, FIG. 6 is a perspective view of FIG. 2, in greater scale and simplified, in which some parts have been omitted for the sake of illustrative simplicity, and FIG. 7 is a horizontal section view according to the line VII—VII of FIG. 3.

DETAILED DESCRIPTION OF THE INVENTION

Referring initially to FIG. 1, the number 1 indicates the wing of a door provided with an anti-panic opening system including, in a generally known manner, an operating bar 2 movable by thrust (in translation or in rotation) to operate the opening of one or more spring latches. The description that follows refers in particular to a lateral spring latch 3 positioned in correspondence with a side of the door 1, and more in particular of the left side with reference to FIG. 1. As will be apparent, the invention also refers to the case in which the spring latch bolt is situated in correspondence with the opposite side, i.e. to the right with reference to FIG. 1.

The spring latch bolt 3 usually co-operates with a stationary locking abutment not shown herein, provided on the frame of the door, and is able to oscillate from an extracted position shown in the drawings, in which it engages said stationary abutment, to a recessed position in which the push opening of the door wing 1 is freed. A needle spring 4 tends normally to maintain the spring latch 3 in the extracted position, and its rotation towards the recessed position is achieved by effect of the actuation by pushing of the control bar 2, whose ends are connected in the way clarified below to a pair of bodies 5a, 5b applied to the door wing 1.

The body 5a, i.e. the one situated on the side of the door corresponding to the spring latch 3, is illustrated in detail in FIGS. 2–7. Said body 5a comprises a support base 6 fastened to a plate 6a which in turn is fastened to the door wing 1 by means of screws 7 and whereon is removably mounted, for instance by means of screws 8, a covering case 9. The base 6 bears an actuator assembly generically indicated as 10, housed within the covering case 9 and arranged to operate the opening of the spring latch 3, in the manner described below. Said spring latch 3 protrudes outside the body 5a through a lateral opening 11 of the covering case 9, provided on the left side thereof. The covering case 9 is also provided with an identical opening 12 (normally closed by means of a removable stopper) formed on its opposite side and usable for the exit of the spring latch 3 from that side, as will become more readily apparent below. In this way the covering case 9 can be used not only for the body 5a but also for the body 5b in the case in which the spring latch 3 is positioned, instead of on the left side, on the right side of the door wing 1.

The covering case 9 inferiorly has a slit 13 through which protrudes an oscillating control lever 14 articulated to the covering case 9 by means of a transverse pivot pin 15. The control lever 14 inferiorly has a slot 16 through which is engaged, in conventional fashion not shown in detail herein, the corresponding end of the bar 2. The opposite end of said bar 2 is borne by an identical oscillating lever 14 borne by the body 5b.

The upper end of the control lever 14 is formed with an appendage 17 which bears against a transverse abutment pivot pin 18 borne by a first movable cursor member 19 mounted able to slide in guided fashion in the lower part of the support base 6. A second movable cursor member 20 is mounted able to slide in guided fashion in the upper part of the support base 6 in a position opposite the first cursor member 19, and bears a transverse abutment pivot pin 21 that is identical to the transverse pin 18.

The two cursor members 19, 20 are mutually coupled kinematically by means of respective integral lateral racks 22, 23 meshed with a central sprocket 24 supported in swivelling fashion by the base 6. In this way to the upward translation of the cursor member 19 corresponds an identical downward translation of the cursor member 20.

The reference number 25 indicates an oscillating lever with two arms mounted on a transverse pivot pin 26 borne by the support base 6 and whose lower arm 27 is connected in rotary fashion in 28 to the first cursor member 19. The second arm of the lever 25, indicated as 29, bears a thrust tooth 30 (more clearly visible in FIG. 7) which bears against a thrust part 31 of the spring latch bolt 3, which in turn is supported in rotary fashion by a vertical pivot pin 32 borne by the support base 6 and whereon the return spring 4 is wound.

A double needle spring 33, also borne by the support base 6, tends to maintain, with its arms 34 and 35 respectively, the cursor member 19 and the cursor member 20 in a mutually distanced position towards the corresponding lower and upper ends of the body 5. This position corresponds to the non actuated condition of the control bar 2 whereto in turn corresponds the resting position of the lever 14 shown in the drawings.

The other body 5b has a simplified structure with respect to the body 5a, because it simply comprises a support base similar to the base 6 and a covering case similar to the covering case 9, but it lacks the actuator assembly 10 with the spring latch 3. The related oscillating control lever 14 therefore serves no other purpose than to support the bar 2.

In operation, when the bar 2 is thrust against the door wing 1 the oscillating levers 14 of the bodies 5a, 5b are rotated (counter-clockwise with reference to FIG. 2), so that the appendage 17 of the lever 14 corresponding to the body 5a causes, acting against the transverse pivot pin 18, the upward translation of the cursor member 19. This causes the rotation (clockwise with reference to FIG. 6) of the two armed lever 25 and thus, by effect of the interaction between the tooth 30 and thrust part 31, the rotation of the spring latch 3 from the extracted position to the recessed position, thereby allowing the opening of the door wing 1 by pushing.

With the described arrangement, the body 5a can be applied instead of the body 5b in the case in which the spring latch bolt 3 needs to be applied on the right side instead of the left side of the door wing 1. In this case it is simply necessary to position the actuator assembly 10 in a condition that is turned over by 180° relative to the one illustrated in the drawings, thereby positioning the spring latch bolt 3 towards the right with the first cursor member 19 situated at the top and the second cursor member 20 situated at the bottom. Having done this, the covering case 9 is fastened to the support base 6 of the assembly 10 thus positioned, arranging the spring latch bolt 3 through the other lateral opening 12. The lateral opening 11 will therefore be able to be closed with a stopper, and the body 5b will be applied in correspondence with the left side of the wing.

With this arrangement, the thrust applied to the bar 2 and the consequent rotation of the control lever 14 of the body 5a causes, by effect of the interaction between the appendage 17 thereof and the abutment pivot pin 21, the upward translation of the second cursor member 20 and the consequent downward translation, by effect of the interaction between the rack 23, the sprocket 24 and the rack 22, of the first cursor member 19. The movement of the spring latch mechanism 3 from the extracted to the recessed position is thus operated similarly to what is described above, by effect of the oscillation of the two armed lever 25 and of the interaction between the tooth 30 and the abutment part 31 of the spring latch 3.

It will be readily apparent from the above that the arrangement of the actuator assembly 10 allows to simplify both the fabrication and the installation of the anti-panic opening system, in particular thanks to the elimination of the need to provide a double spring latch and related double actuator assembly.

Naturally, the construction details and the embodiments may be widely varied from what is described and illustrated herein, without thereby departing from the scope of the present invention as defined in the claims that follow.

What is claimed is:

1. An anti-panic opening system for door, including a control bar (2) applied transversely to the wing of the door (1) and movable by a pushing action to actuate opening of a lateral spring latch bolt (3) movable between an extracted locking position and a recessed position to free the push opening of the door (1), in which said spring latch (3) is operated by means of an actuator assembly (10) housed within a covering case (9) and including a control lever (14) movable by means of said bar (2), wherein;

said actuator assembly (10) includes a first and a second movable actuating member (19, 20) operable respectively in a first position in which said spring latch (3) projects from a first side of the covering case (9) and in a second position, turned over by 180° relative to said first position, in which said spring latch (3) projects from a second side, opposite from said first side of the covering case (9), said control lever (14) is connected in articulated fashion to said covering case (9), and said covering case(9) can be coupled to said actuator assembly (10) selectively in one or in the other of said first and second position thereof and has two lateral openings (11, 12) usable correspondingly for the passage of said spring latch (3), wherein said first and second movable members consist of a pair opposite cursors (19, 20) mounted in sliding fashion along a guiding support (6) of said actuator assembly (10) and kinematically coupled to each other in such a way that to the translation of one of said cursors (19) in a direction corresponds the translation of the other of said cursors (20) in the opposite direction; each of said cursors (19, 20) being provided with a respective abutment element (18, 21) able to co-operate with said control lever.

2. System as claimed in claim 1, wherein said cursors (19, 20) are formed with respective racks (22, 23) meshed from opposite parts with a transmission sprocket (24) borne by said guiding support (6).

3. System as claimed in claim 1, wherein said cursors (19, 20) operate said spring latch (3) by means of a common oscillating thrust member (25).

* * * * *